United States Patent [19]

Coleman

[11] 4,189,610

[45] Feb. 19, 1980

[54] PREPARATION OF 4,4-DIOXY-SUBSTITUTED STILBENES

[75] Inventor: James P. Coleman, Maryland Heights, Mo.

[73] Assignee: Monsanto Company, St. Louis, Mo.

[21] Appl. No.: 846,753

[22] Filed: Oct. 31, 1977

[51] Int. Cl.$^2$ .................. C07C 39/22; C07C 43/20
[52] U.S. Cl. .................. 568/646; 560/138; 568/636; 568/637; 568/644; 568/645; 568/729
[58] Field of Search .............. 568/729, 636, 637, 645, 568/646; 260/613 A; 560/138

[56] References Cited

U.S. PATENT DOCUMENTS

| | | | |
|---|---|---|---|
| 3,444,245 | 5/1969 | Sieber | 260/613 A |
| 3,624,162 | 11/1971 | Sieber | 568/729 |
| 3,683,009 | 8/1972 | Middleton | 260/613 A |

OTHER PUBLICATIONS

Sieber, Ann. 730, 31–46 (1969).

*Primary Examiner*—Jane S. Myers
*Attorney, Agent, or Firm*—Wendell W. Brooks; J. W. Williams, Jr.; J. D. Kennedy

[57] ABSTRACT

Dehydrohalogenation-rearrangement of 1,1-bis(4-oxy-substituted aryl)-2-haloethanes to yield 4,4'-dioxysubstituted stilbenes is effected by heating an acidic reaction medium comprising the 1,1-bis(4-oxy-substituted aryl)-2-haloethane dissolved in a solution of an aliphatic carboxylic acid and a carboxylic acid salt. The process is particularly directed to the preparation of 4,4'-dihydroxystilbene from 1,1-bis(4-hydroxyphenyl)-2-chloroethane.

21 Claims, No Drawings

PREPARATION OF 4,4-DIOXY-SUBSTITUTED STILBENES

BACKGROUND OF THE INVENTION

This invention relates to the preparation of 4,4'-dioxy-substituted stilbenes. More specifically, it relates to a dehydrohalogenation-rearrangement of 1,1-bis(4-oxy-substituted aryl)-2-haloethanes under acidic reaction conditions to yield 4,4'-dioxy-substituted stilbenes, particularly 4,4'-dihydroxystilbene from 1,1-bis(4-hydroxyphenyl)-2-chloroethane.

The dehydrohalogenation-rearrangement of 1,1-bis(4-hydroxyaryl)-2-haloethanes to 4,4'-dihydroxystilbenes is known in the art. The reaction is effected under strongly basic and rather drastic conditions by heating the compound in a solution of potassium hydroxide or sodium hydroxide in methanol or ethanol at the boiling point of the solvent, followed by further heating of the dehydrohalogenated product in a high-boiling solvent selected from the group consisting of ethylene glycol, diethylene glycol monomethyl ether (methyl carbitol), and nitrobenzene to the boiling point of such solvent. The reaction may also be effected in one step by heating the 1,1-bis(4-hydroxyaryl)-2-haloethane directly in a solution of potassium hydroxide or sodium hydroxide in a high-boiling solvent selected from the above list. These processes of preparing 4,4'-dihydroxystilbenes are disclosed in Sieber, U.S. Pat. No. 3,624,162. However, they involve the difficult isolation of the desired stilbene from a high-boiling solvent, a factor which significantly decreases the commercial attractiveness and adaptability of the processes.

The disadvantages encountered in the strongly basic, high-boiling solvent processes of the prior art are overcome by the discovery that the dehydrohalogenation-rearrangement of 1,1-bis(4-oxy-substituted aryl)-2-haloethanes can be readily accomplished under acidic reaction conditions to yield 4,4'-dioxy-substituted stilbenes.

SUMMARY OF THE INVENTION

According to the present invention, it has been discovered that 4,4'-dioxy-substituted stilbenes can be readily prepared from 1,1-bis(4-oxy-substituted aryl)-2-haloethanes under acidic reaction conditions. The process comprises heating an acidic reaction medium comprising a 1,1-bis(4-oxy-substituted aryl)-2-haloethane dissolved in a solution of an aliphatic carboxylic acid and a carboxylic acid salt to a temperature, and for a time, sufficient to cause dehydrohalogenation-rearrangement of the 1,1-bis(4-oxy-substituted aryl)-2-haloethane to yield the 4,4'-dioxy-substituted stilbene.

The 4,4'-dioxy-substituted stilbene products obtained in the present process can be recovered by any number of well-known and conventional procedures in any desirably convenient form. For example, 4,4'-dihydroxystilbene can be isolated as the free dihydroxy compounds or derivatives thereof such as the corresponding diacyloxy compounds, while 4,4'-dialkoxystilbenes can be conveniently isolated as dialkoxy compounds.

DETAILED DESCRIPTION OF THE INVENTION

Dehydrohalogenation-rearrangement of 1,1-bis(4-oxy-substituted aryl)-2-haloethanes to yield 4,4'-dioxy-substituted stilbenes can be accomplished under acidic reaction conditions.

In accordance with the present process, an acidic reaction medium comprising the 1,1-bis(4-oxy-substituted aryl)-2-haloethane dissolved in a solution of aliphatic carboxylic acid and a carboxylic acid salt is heated to a temperature, and for a time, sufficient to cause dehydrohalogenation-rearrangement of the 1,1-bis(4-oxy-substituted aryl)-2-haloethane to yield the 4,4'-dioxy-substituted stilbene.

Suitable 1,1-bis(4-oxy -substituted aryl)-2-haloethanes which can be used to effect the dehydrohalogenation rearrangement according to the present process are in general represented by the formula:

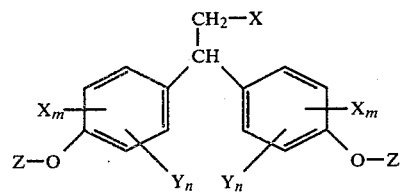

in which X independently represents a halogen selected from the group consisting of chlorine, bromine, and iodine; Y independently represents a non-interfering hydrocarbyl group, including, for example, lower alkyl of 1 to 6 carbon atoms and phenyl; Z represents hydrogen or Y; and m and n each independently represent an integer from zero (0) to 4, inclusive, with the proviso that the sum of m and n, with respect to each aryl ring does not exceed 4.

The term "non-interfering hydrocarbyl group" is employed herein to mean a hydrocarbon group which can be present in the 1,1-bis(4-hydroxyaryl)-2-haloethane without rendering the dehydrohalogenation-rearrangement reaction substantially inoperative under process conditions. Such groups, as noted hereinabove, include lower alkyl of 1 to 6 carbon atoms and phenyl.

Of the halogens present in the 1,1-bis(4-oxy-substituted aryl)-2-haloethane, chlorine is generally preferred in that it is relatively less expensive, and, in the event, subsequent hydrogenation of a halogen-containing 4,4'-dioxy-substituted stilbene to the corresponding 1,2-(4-oxy-substituted aryl)ethane is desired, such compounds, as organochlorides, exhibit less tendency to deactivate or poison the hydrogenation catalyst.

Representative of the 1,1-bis(4-oxy-substituted aryl)-2-haloethanes suitable for use in the present process are 1,1-bis(4-hydroxyphenyl)-2-chloroethane, 1,1-bis(4-hydroxy-phenyl)-2-bromoethane, 1,1-bis(4-hydroxyphenyl)-2-iodoethane, 1,1-bis(4-methoxyphenyl)-2-chloroethane, 1,1-bis(4-methoxyphenyl)-2-bromoethane, 1,1-bis(4-methoxyphenyl)-2-iodoethane, 1,1-bis(4-ethoxyphenyl)-2-chloroethane, 1,1-bis(4-ethoxyphenyl)-2-bromoethane, 1,1-bis(4-ethoxyphenyl)-2-iodoethane, 1,1-bis(4-hydroxy-2-methylphenyl)-2-chloroethane, 1,1-bis(4-hydroxy-2-methylphenyl)-2-bromoethane, 1,1-bis(4-hydroxy-2-methylphenyl)-2-iodoethane, 1,1-bis(4-methoxy-2-methylphenyl)-2-chloroethane, 1,1-bis(4-methoxy-2-methylphenyl)-2-bromoethane, 1,1-bis(4-methoxy-2-methylphenyl)-2-iodoethane, 1,1-bis(4-ethoxy-2-methylphenyl)-2-chloroethane, 1,1-bis(4-ethoxy-2-methylphenyl)-2-bromoethane, 1,1-bis(4-ethoxy-2-methylphenyl)-2-iodoethane, 1,1-bis(4-hydroxy-3-methylphenyl)-2-chloroethane, 1,1-bis(4-hydroxy-3-methylphenyl)-2- bromoethane, 1,1-bis(4-hydroxy-3-methylphenyl)-2-iodoethane, 1,1-bis(4-methoxy-3-methylphenyl)-2-chloroethane, 1,1-bis(4-methoxy-3-methylphenyl)-2-bromoethane, 1,1-bis(4-methoxy-3-methylphenyl)-2-iodoethane, 1,1-bis(4-ethoxy-3-methylphenyl)-2-chloroethane, 1,1-bis(4-ethoxy-3-methylphenyl)-2-bromoethane 1,1-bis(4-ethoxy-3-methylphenyl)-2-iodoethane, 1,1-bis(2,3-dimethyl-4-hydroxyphenyl)-2-chloroethane, 1,1-bis(2,3-dimethyl-4-hydroxyphenyl)-2-bromoethane, 1,1-bis(2,3-dimethyl-4-hydroxyphenyl)-2-iodoethane, 1,1-bis(2,3-dimethyl-4-methoxyphenyl)-2-chloroethane, 1,1-bis(2,3-dimethyl-4-methoxyphenyl)-2-bromoethane, 1,1-bis(2,3-dimethyl-4-methoxyphenyl)-2-iodoethane, 1,1-bis(2,3-dimethyl-4-ethoxyphenyl)-2-chloroethane, 1,1-bis(2,3-dimethyl-4-ethoxyphenyl)-2-bromoethane, 1,1-bis(2,3-dimethyl-4-ethoxyphenyl)-2-iodoethane, 1,1-bis(2,5-dimethyl-4-hydroxyphenyl)-2-chloroethane, 1,1-bis(2,5-dimethyl-4-hydroxyphenyl)-2-bromoethane, 1,1-bis(2,5-dimethyl-4-hydroxyphenyl)-2-iodoethane, 1,1-bis(2,5-dimethyl-4-methoxyphenyl)-2-chloroethane, 1,1-bis(2,5-dimethyl-4-methoxyphenyl)-2-bromoethane, 1,1-bis(2,5-dimethyl-4-methoxyphenyl)-2-iodoethane, 1,1-bis(2,5-dimethyl-4-ethoxyphenyl)-2-chloroethane, 1,1-bis(2,5-dimethyl-4-ethoxyphenyl)-2-bromoethane, 1,1-bis(2,5-dimethyl-4-ethoxyphenyl)-2-iodoethane, 1,1-bis-(2,6-dimethyl-4-hydroxyphenyl-2-chloroethane, 1,1-bis(2,6-dimethyl-4-hydroxyphenyl)-2-bromoethane, 1,1-bis(2,6-dimethyl-4-hydroxyphenyl)-2-iodoethane, 1,1-bis(2,6-dimethyl-4-methoxyphenyl)-2-chloroethane, 1,1-bis(2,6-dimethyl-4-methoxyphenyl)-2-bromoethane, 1,1-bis(2,6-dimethyl-4-methoxyphenyl)-2-iodoethane, 1,1-bis(2,6-dimethyl-4-ethoxyphenyl)-2-chloroethane, 1,1-bis(2,6-dimethyl-4-ethoxyphenyl)-2-bromoethane, 1,1-bis(2,6-dimethyl-4-ethoxyphenyl)-2-iodoethane, 1,1-bis(3,5-dimethyl-4-hydroxyphenyl)-2-chloroethane, 1,1-bis(3,5-dimethyl-4-hydroxyphenyl)-2-bromoethane, 1,1-bis(3,5-dimethyl-4-hydroxyphenyl)-2-iodoethane, 1,1-bis(3,5-dimethyl-4-methoxyphenyl)-2-chloroethane, 1,1-bis(3,5-dimethyl-4-methoxyphenyl)-2-bromoethane, 1,1-bis(3,5-dimethyl-4-methoxyphenyl)-2-iodoethane, 1,1-bis(3,5-dimethyl-4-ethoxyphenyl)-2-chloroethane, 1,1-bis(3,5-dimethyl-4-ethoxyphenyl)-2-bromoethane, 1,1-bis(3,5-dimethyl-4-ethoxyphenyl)-2-iodoethane, 1,1-bis(3,6-dimethyl-4-hydroxyphenyl)-2-chloroethane, 1,1-bis(3,6-dimethyl-4-hydroxyphenyl)-2-bromoethane, 1,1-bis(3,6-dimethyl-4-hydroxyphenyl-2-iodoethane, 1,1-bis(3,6-dimethyl-4-methoxyphenyl)-2-chloroethane, 1,1-bis(3,6-dimethyl-4-methoxyphenyl)-2-bromoethane, 1,1-bis(3,6-dimethyl-4-methoxyphenyl)-2-iodoethane, 1,1-bis(3,6-dimethyl-4-ethoxyphenyl-2-chloroethane, 1,1-bis(3,6-dimethyl-4-ethoxyphenyl)-2-bromoethane, 1,1-bis(3,6-dimethyl-2-ethoxyphenyl)-2-iodoethane, 1,1-bis(2,3-diethyl-4-hydroxyphenyl)-2-chloroethane, 1,1-bis(2,3-diethyl-4-hydroxyphenyl)-2-bromoethane, 1,1-bis(2,3-diethyl-4-hydroxyphenyl)-2-iodoethane, 1,1-bis-(2,3-diethyl-4-methoxyphenyl)-2-chloroethane, 1,1-bis(2,3-diethyl-4-methoxyphenyl)-2-bromoethane, 1,1-bis(2,3-diethyl-4-methoxyphenyl)-2-iodoethane, 1,1-bis(2,3-diethyl-4-ethoxyphenyl)-2-chloroethane, 1,1-bis(2,3-diethyl-4-ethoxyphenyl)-2-bromoethane, 1,1-bis(2,3-diethyl-4-ethoxyphenyl)-2-iodoethane, 1,1-bis(2,5-diethyl-4-hydroxyphenyl)-2-chloroethane, 1,1-bis-(2,5-diethyl-4-hydroxyphenyl)-2-bromoethane, 1,1-bis(2,5-diethyl-4-hydroxyphenyl)-2-iodoethane, 1,1-bis(2,5-diethyl-4-methoxyphenyl)-2-chloroethane, 1,1-bis(2,5-diethyl-4-methoxyphenyl)-2-bromoethane, 1,1-bis(2,5-diethyl-4-methoxyphenyl)-2-iodoethane, 1,1-bis(2,5-diethyl-4-ethoxyphenyl)-2-chloroethane, 1,1-bis(2,5-diethyl-4-ethoxyphenyl)-2-bromoethane, 1,1-bis(2,5-diethyl-4-ethoxyphenyl)-2-iodoethane, 1,1-bis(2,6-diethyl-4-hydroxyphenyl)-2-chloroethane, 1,1-bis(2,6-diethyl-4-hydroxyphenyl)-2-bromoethane, 1,1-bis(2,6-diethyl-4-hydroxyphenyl)-2-iodoethane, 1,1-bis(2,6-diethyl-4-methoxyphenyl)-2-chloroethane, 1,1-bis(2,6-diethyl-4-methoxyphenyl)-2-bromoethane, 1,1-bis(2,6-diethyl-4-methoxyphenyl)-2-iodoethane, 1,1-bis(2,6-diethyl-4-ethoxyphenyl)-2-chloroethane, 1,1-bis(2,6-diethyl-4-ethoxyphenyl)-2-bromoethane, 1,1-bis(2,6-diethyl-4-ethoxyphenyl)-2-iodoethane, 1,1-bis(3,5-diethyl-4-hydroxyphenyl)-2-chloroethane, 1,1-bis(3,5-diethyl-4-hydroxyphenyl)-2-bromoethane, 1,1-bis-(3,5-diethyl-4-hydroxyphenyl)-2-iodoethane, 1,1-bis(3,5-diethyl-4-methoxyphenyl)-2-chloroethane, 1,1-bis(3,5-diethyl-4-methoxyphenyl)-2-bromoethane, 1,1-bis(3,5-diethyl-4-methoxyphenyl)-2-iodoethane, 1,1-bis(3,5-diethyl-4-ethoxyphenyl)-2-chloroethane, 1,1-bis(3,5-diethyl-4-ethoxyphenyl)-2-bromoethane, 1,1-bis(3,5-diethyl-4-ethoxyphenyl)-2-iodoethane, 1,1-bis(3,6-diethyl-4-hydroxyphenyl)-2-chloroethane, 1,1-bis(3,6-diethyl-4-hydroxyphenyl)-2-bromoethane, 1,1-bis(3,6-diethyl-4-hydroxyphenyl)-2-iodoethane, 1,1-bis(3,6-diethyl-4-methoxyphenyl)-2-chloroethane, 1,1-bis(3,6-diethyl-4-methoxyphenyl)-2-bromoethane, 1,1-bis(3,6-diethyl-4-methoxyphenyl)-2-iodoethane, 1,1-bis-(3,6-diethyl-4-ethoxyphenyl)-2-chloroethane, 1,1-bis(3,6-diethyl-4-ethoxyphenyl)-2-bromoethane, 1,1-bis(3,6-diethyl-4-ethoxyphenyl)-2-iodoethane, 1,1-bis(3,5-di-t-butyl-4-hydroxyphenyl)-2-chloroethane, 1,1-bis(3,5-di-t-butyl-4-hydroxyphenyl)-2-bromoethane, 1,1-bis(3,5-di-t-butyl-4-hydroxyphenyl)-2-iodoethane, 1,1-bis(3,5-di-t-butyl-4-methoxyphenyl)-2-chloroethane, 1,1-bis(3,5-di-t-butyl-4-methoxyphenyl)-2-bromoethane, 1,1-bis(3,5-di-t-butyl-4-methoxyphenyl)-2-iodoethane, 1,1-bis(3,5-di-t-butyl-4-ethoxyphenyl)-2-chloroethane, 1,1-bis(3,5-di-t-butyl-4,-ethoxyphenyl)-2-bromoethane, 1,1-bis(3,5-di-t-butyl-4-ethoxyphenyl)-2-iodoethane, 1,1-bis(4-hydroxy-2,3,5-trimethylphenyl)-2-chloroethane, 1,1-bis(4-hydroxy-2,3,5-trimethylphenyl)-2-bromoethane, 1,1-bis(4-hydroxy-2,3,5-trimethylphenyl)-2-iodoethane, 1,1-bis(4-methoxy-2,3,5-trimethylphenyl)-2-chloroethane, 1,1-bis(4-methoxy-2,3,5-trimethylphenyl)-2-bromoethane, 1,1-bis(4-methoxy-2,3,5-trimethylphenyl)-2-iodoethane, 1,1-bis(4-ethoxy-2,3,5-trimethylphenyl)-2-chloroethane, 1,1-bis(4-ethoxy-2,3,5-trimethylphenyl)-2-bromoethane, 1,1-bis(4-ethoxy-2,3,5-trimethylphenyl)-2-iodoethane, 1,1-bis(4-hydroxy-2,3,6-trimethylphenyl)-2-chloroethane, 1,1-bis(4-hydroxy-2,3,5-trimethylphenyl)-2-bromoethane, 1,1-bis(4-hydroxy-2,3,6-trimethylphenyl)-2-iodoethane, 1,1-bis(4-methoxy-2,3,6-trimethylphenyl)-2-chloroethane, 1,1-bis(4-methoxy-2,3,6-trimethylphenyl)-2-bromoethane, 1,1-bis(4-methoxy-2,3,6-trimethylphenyl)-2-iodoethane, 1,1-bis(4-ethoxy-2,3,6-trimethylphenyl)-2-chloroethane, 1,1-bis(4-ethoxy-2,3,6-trimethylphenyl)-2-bromoethane, 1,1-bis(4-ethoxy-2,3,6-trimethylphenyl)-2-iodoethane, 1,1-bis(2,3-dimethyl-5-ethyl-4-hydroxyphenyl)-2-chloroethane, 1,1-bis(2,3-dimethyl-5-ethyl-4-hydroxyphenyl)-2-bromoethane, 1,1-bis-2,3-dimethyl-5-ethyl-4-hydroxyphenyl)-2-iodoethane, 1,1-bis-2,3-dimethyl-5-ethyl-4-methoxyphenyl)-2-chloroethane, 1,1-bis-(2,3-dimethyl-5-ethyl-4-methoxyphenyl)-2-bromoethane, 1,1-bis(2,3-dimethyl-5-ethyl-4-methoxyphenyl)-2-iodoethane, 1,1-bis(2,3-dimethyl-4-ethoxy-5-ethylphenyl)-2-chloroethane, 1,1-bis(2,3-dimethyl-4-ethoxy-5-ethylphenyl)-2-bromoethane, 1,1- bis(2,3-dimethyl-4-ethoxy-5-ethylphenyl)-2-iodoethane, 1,1-bis(2,5-dimethyl-3-ethyl-4-hydroxyphenyl)-2-chloroethane, 1,1-bis(2,5-dimethyl-3-ethyl-4-hydroxyphenyl)-2-bromoethane, 1,1-bis(2,5-dimethyl-3-ethyl-4-hydroxyphenyl)-2-iodoethane, 1,1-bis(2,5-dimethyl-3-ethyl-4-methoxyphenyl)-2-chloroethane, 1,1-bis(2,5-dimethyl-3-ethyl-4-methoxyphenyl)-2-bromoethane, 1,1-bis(2,5-dimethyl-3-ethyl-4-methoxyphenyl)-2-iodoethane, 1,1-bis(2,5-dimethyl-4-ethoxy-3-ethylphenyl)-2-chloroethane, 1,1-bis(2,5-dimethyl-4-ethoxy-3-ethylphenyl)-2-bromoethane, 1,1-bis(2,5-dimethyl-4-ethoxy-3-ethylphenyl)-2-iodoethane, 1,1-bis-(2-chloro-4-hydroxyphenyl)-2-chloroethane, 1,1-bis(2-chloro-4-hydroxyphenyl)-2-bromoethane, 1,1-bis(2-chloro-4-hydroxyphenyl)-2-iodoethane, 1,1-bis(2-chloro-4-methoxyphenyl)-2-chloroethane, 1,1-bis(2-chloro-4-methoxyphenyl)-2-bromoethane, 1,1-bis(2-chloro-4-methoxyphenyl)-2-iodoethane, 1,1-bis(2-chloro-4-ethoxyphenyl)-2-chloroethane, 1,1-bis(2-chloro-4-ethoxyphenyl)-2-bromoethane, 1,1-bis(2-chloro-4-ethoxyphenyl)-2-iodoethane, 1,1-bis(2-bromo-4-hydroxyphenyl)-2-chloroethane, 1,1-bis(2-bromo-4-hydroxyphenyl)-2-bromoethane, 1,1-bis(2-bromo-4-hydroxyphenyl-2-iodoethane, 1,1-bis(2-bromo-4-methoxyphenyl)-2-chloroethane, 1,1-bis(2-bromo-4-methoxyphenyl)-2-bromoethane, 1,1-bis(2-bromo-4-methoxyphenyl)-2-iodoethane, 1,1-bis(2-iodo-4-hydroxyphenyl)-2-chloroethane, 1,1-bis(2-iodo-4-hydroxyphenyl)-2-bromoethane, 1,1-bis(2-iodo-4-hydroxyphenyl)-2-iodoethane, 1,1-bis(2-iodo-4-methoxyphenyl)-2-chloroethane, 1,1-bis(2-iodo-4-methoxyphenyl)-2-bromoethane, 1,1-bis(2-iodo-4-methoxyphenyl)-2-iodoethane, 1,1-bis)4-ethoxy-2-iodophenyl)-2-chloroethane, 1,1-bis(4-ethoxy-2-iodophenyl)-2-bromoethane, 1,1-bis(4-ethoxy-2-iodophenyl)-2-iodoethane, 1,1-bis(4-hydroxy-2,3,5,6-tetramethylphenyl)-2-chloroethane, 1,1-bis(4-hydroxy-2,3,5,6-tetramethylphenyl)-2-bromoethane, 1,1-bis(4-hydroxy-2,3,5,6-tetramethylphenyl)-2-iodoethane, 1,1-bis(4-methoxy-2,3,5,6-tetramethylphenyl)-2-chloroethane, 1,1-bis(4-methoxy-2,3,5,6-tetramethylphenyl)-2-bromoethane, 1,1-bis(4-methoxy-2,3,5,6-tetramethylphenyl)-2-iodoethane, 1,1-bis(4-ethoxy-2,3,5,6-tetramethylphenyl)-2-chloroethane, 1,1-bis(4-ethoxy-2,3,5,6-tetramethylphenyl)-2-bromoethane, 1,1-bis(4-ethoxy-2,3,5,6-tetramethylphenyl)-2-iodoethane, and the like.

Other compounds similarly oriented with respect to the relative positions of the 2-haloethane moiety and the oxy substituent but having a different numbering designation because of rules of nomenclature are also suitable for use in the present process. Such compounds include those wherein the X substituent on each aryl ring represents a different halogen, and phenyl substituted compounds, for example, biphenyls. Illustrative examples include 1-(3-bromo-4-hydroxyphenyl)-1-3(chloro-4-hydroxyphenyl)-2-chloroethane, 1-(3-bromo-4-hydroxyphenyl)-2-(3-chloro-4-hydroxyphenyl)-2-bromoethane, 1-(3-bromo-4-hydroxyphenyl)-1-(3-chloro-4-hydroxyphenyl)-2-iodoethane, 1,1-bis-[2-(5-hydroxybiphenyl)]-2-chloroethane [1,1-bis(4-hydroxy-2-phenylphenyl)-2-chloroethane], 1,1-bis[2-(5-hydroxybiphenyl)]-2-bromoethane [1,1-bis(4-hydroxy-2-phenylphenyl)-2-bromoethane], 1,1-bis[2-5-hydroxyphenyl)]-2-iodoethane [1,1-bis(4-hydroxy-2-phenylphenyl)-2-iodoethane], 1,1-bis[2-(5-methoxybiphenyl)]-2-chloroethane [1,1-bis(4-methoxy-2-phenylphenyl)-2-chloroethane], 1,1-bis[2-(5-methoxybiphenyl)]-2-bromoethane [1,1-bis(4-methoxy-2-phenylphenyl)-2-bromoethane], 1,1-bis[2-(5-methoxybiphenyl)]-2-iodoethane [1,1-bis(4-methoxy-2-phenylphenyl-2-iodoethane], and the like.

Of the compounds suitable for use in the present process, the 1,1-bis(4-hydroxyphenyl)-2-haloethanes are of particular importance in that the product therefrom, 4,4'-dihydroxystilbene, by virtue of its extremely potent estrogenic activity, has a definite significance in biology, physiology, and biochemistry. Of these, 1,1-bis(4-hydroxyphenyl)-2-chloroethane is especially important in that its preparation is accomplished without incurring any undue and unnecessary expense.

As indicated hereinbelow the preparation of the present process is carried out by heating an acidic reaction medium comprising the 1,1-bis(4-oxy-substituted aryl)-2-haloethane dissolved in a solution of an aliphatic carboxylic acid and a carboxylic acid salt to a temperature, usually between about 100° C. and 250° C., and for a time, in general between about 0.5 hours and about 5 hours for substantially complete reaction in batch operation, sufficient to cause dehydrohalogenation-rearrangement of the 1,1-bis(4-oxy-substituted aryl)-2-haloethane to yield the 4,4'-dioxy-substituted stilbene product. It will of course be recognized that continous operations are not so restricted in that unreacted starting material can be recycled for further reaction.

The reaction of the present invention can in general be illustrated:

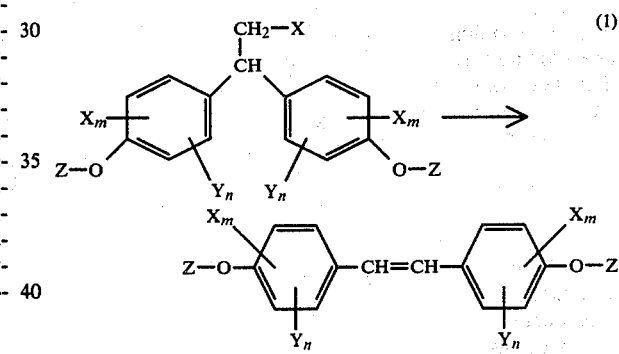

in which X, Y, Z, and m and n are as defined hereinabove. Equation (2) illustrates a specific embodiment of the present invention, the preparation of 4,4'-dihydroxystilbene via dehydrohalogenation-rearrangement of 1,1-bis(4-hydroxyphenyl)-2-chloroethane.

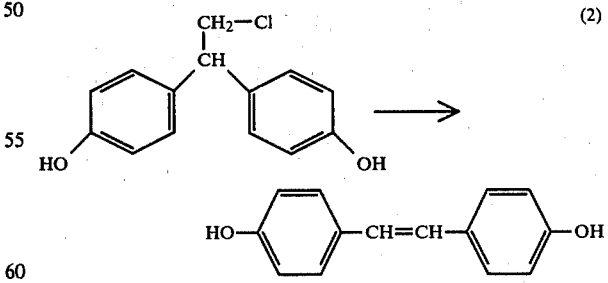

The aliphatic carboxylic acids desirable for use in the present invention must be compatible with the present process. That is, the carboxylic acid (a) should be inert under reaction conditions; (b) should dissolve the 1,1-bis(4-oxy-substituted aryl)-2-haloethane starting material; and (c) should dissolve the carboxylic acid salt, all of which are preferred. Carboxylic acid solvents which satisfy these preferred requirements permit the desired dehydrohalogenation-rearrangement of the 1,1-bis(4-oxy-substituted aryl)-2-haloethane to yield the corresponding 4,4'-dioxy-substituted stilbenes to proceed at a reasonable rate without complications and difficulties. In addition, the carboxylic acid solvent preferably should be substantially anhydrous. It will be noted, however, that small amounts of water within the range of about 10 percent or lower to about 15 percent cause no adverse effects upon the course and yield of the reaction, and solvents containing such amounts of water are suitable.

Exemplary of the aliphatic carboxylic acids which meet these requirements are the $C_2$ to $C_6$ aliphatic carboxylic acids. Of these, those preferred are $C_2$ and $C_3$ carboxylic acids, with the $C_2$ aliphatic carboxylic acid, acetic acid, being most preferred in that it is relatively inexpensive and readily available in substantially anhydrous form.

The acidic reaction medium must contain carboxylic acid salt. The salt preferably is soluble in the aliphatic carboxylic acid employed as solvent to form a homogeneous solution thereof. Exemplary of such salts are the alkali metal—lithium, sodium, potassium, rubidium, and cesium—carboxylic acid salts, the alkaline earth metal—magnesium, calcium, and barium—carboxylic acid salts, and quaternary ammonium—tetramethylammonium, tetraethylammonium, tetra-n-propylammonium, tetra-n-butylammonium, n-butyltri-n-propylammonium, and the like—carboxylic acid salts. The alkaline earth metal salts and the quaternary ammonium salts, however, are generally more expensive and usually offer no particular advantage over the alkali metal carboxylic acid salts.

While any carboxylic acid salt can in general be employed so long as it is sufficiently soluble in the aliphatic carboxylic acid and causes no adverse side reactions, it is preferred to employ the alkali metal salts of the $C_2$ to $C_6$ aliphatic carboxylic acids employed. And further, it is found in practice that the alkali metal carboxylic acid salts corresponding to the aliphatic carboxylic acid employed as solvent is most preferred. Thus, since acetic acid is the most preferred aliphatic carboxylic acid, the alkali metal acetates, particularly sodium acetate, are the most preferred salts.

It will be apparent to those skilled in the art that the pre-formed carboxylic acid salt can be employed. However, when the carboxylic acid salt is that which corresponds to the aliphatic carboxylic acid being employed, it can either be charged directly—that is, as the pre-formed salt—to the carboxylic acid, or alternatively, it can be formed in situ by charging an anhydrous hydroxide ion-containing compound. The cation of such compounds should preferably be an alkali metal ion, an alkaline earth metal ion, or a quaternary ammonium ion. Thus the carboxylic acid salt can be formed in situ by charging an alkali metal hydroxide, such as, for example, lithium hydroxide, sodium hydroxide, potassium hydroxide, rubidium hydroxide, and cesium hydroxide, an alkaline earth metal hydroxide, such as, for example, magnesium hydroxide, calcium hydroxide, and barium hydroxide, or a quaternary ammonium hydroxide, such as, for example, tetraethylammonium hydroxide, tetra-n-propylammonium hydroxide, tetra-n-butylammonium hydroxide, in appropriate amounts to the aliphatic carboxylic acid. For example, when glacial acetic acid is the aliphatic carboxylic acid, the charging of sodium hydroxide thereto produces sodium acetate in situ in an amount equivalent to the amount (gram-equivalent weights) of added sodium hydroxide.

Of the hydroxides suitable for use in the present process, the alkali metal hydroxides are preferred. Of these, sodium hydroxide is most preferred in that the resulting sodium salt is in general highly soluble in the corresponding aliphatic carboxylic acid. Moreover, sodium hydroxide is relatively inexpensive and readily available.

The concentration of the 1,1-bis(4-oxy-substituted aryl)-2-haloethane employed in the process of the present invention is not extremely critical, although it will be noted that extremely high concentrations tend to cause a decrease in the yield of the desired 4,4'-dioxy-substituted stilbene products. In general, however, all that is necessary is that sufficient amounts be present in solution in the acidic reaction medium to permit the dehydrohalogenation-rearrangement thereof to yield the corresponding 4,4'-dioxy-substituted silbene to proceed at a reasonable rate. Thus, although concentrations as low as 0.01 percent by weight, or even lower, in the acidic reaction medium can be employed, for reasons of efficiency and economy, it is preferred to employ concentrations of between about 5 percent and about 20 percent by weight, or on a molar basis, between about 0.2 molar to about 0.8 molar, or even higher, of the 1,1-bis(4-oxy-substituted aryl)-2-haloethane.

The concentration of the carboxylic acid salt is determined in the first instance by the corresponding concentration of the 1,1-bis(4-oxy-substituted aryl)-2-haloethane employed. That is, for complete stoichiometric reaction, the concentration of the carboxylic acid salt must be present at least in the same gram-equivalent weight quantity (with respect to the aliphatic carboxylic acid anion) as the 1,1-bis(4-oxy-substituted aryl)-2-haloethane. Thus the gram-equivalent weight ratio of carboxylic acid salt to the 1,1-bis(4-oxy-substituted aryl)-2-haloethane is preferably at least 1:1. A slight excess, however, on the order of about 10 percent, may be beneficial. On the other hand, a less than 1:1 gram equivalent weight ratio may cause unwanted side reactions to occur, and thereby reduce both the yield and purity of the desired 4,4'-dioxy-substituted stilbene product.

The reaction conditions employed in the present process can vary within fairly wide limits. It will, of course, be recognized that the present process is temperature dependent in the sense that the reaction proceeds at an increased rate at higher temperatures. Excessively high temperatures, however, are to be avoided in that the selectivity of the desired 4,4'-dioxy-substituted stilbene product may be adversely affected. Suitable temperatures will in general range from about 100° C. to about 250° C., with temperatures between about 120° C. and about 225° C. being preferred. At the preferred temperatures the reaction proceeds in a smooth manner and at a reasonable rate to yield the 4,4'-dioxy-substituted stilbene product.

The time required for the desired dehydrohalogenation-rearrangement to occur is not critical. Generally, a reaction time between about 0.5 hours and about 5 hours is required for complete reaction for batch operations, with about 3 hours usually being sufficient. It will, of course, be recognized, however, that the actual reaction time will vary with the 1,1-bis(4-oxy-substituted aryl)-2-haloethane starting material and its concentration, temperature, the mode of operation and the like employed.

The present process can be conducted at atmospheric pressure, super atmospheric pressures, and subatmospheric pressures. In certain instances, superatmospheric pressures may be advantageously employed in that reaction times may be substantially decreased. However, it will be recognized that in certain instances, atmospheric pressure may be preferred for reasons of economy and ease of construction of reaction equipment.

The process of the present invention can be conducted under an inert atmosphere, if desired, and in certain instances may actually be preferred. When an inert atmosphere is desired, dry nitrogen gas admirably serves the purpose. It may simply be passed through the reaction mixture when the process is conducted at atmospheric pressure, or it may be employed to pressurize the reaction vessel to the desired pressure when the process is conducted at super atmospheric pressures. Suitable super atmospheric pressures range between about 75 psig and about 150 psig, although as noted hereinabove, any desired pressure may be employed.

The present process is suited to either batch or continuous operations. Continuous operations can involve recirculation of the aliphatic carboxylic acid and unreacted 1,1-bis(4-oxy-substituted aryl)-2-haloethane starting material following isolation of the 4,4'-dioxy-substituted stilbene product. Additional 1,1-bis(4-oxy-substituted aryl)-2-haloethane starting material as well as carboxylic acid salt can then be charged to the reaction vessel to continue the process in a subsequent reaction.

The 4,4'-dioxy-substituted stilbene products obtained in the present process can be readily recovered by any number of well-known and conventional procedures. It will be understood, however, that the isolation procedures employed in the procedural examples and discussed hereinbelow are primarily for illustrative purposes. Other procedures can be employed, and may be preferred, for commercial use.

Upon completion of the reaction, the aliphatic carboxylic acid and unreacted oxy-substituted arene, (if crude 1,1-bis(4-oxy-substituted aryl)-2-haloethane, prepared from an appropriate oxy-substituted arene, for example, phenol, and a monohaloacetaldehyde, is employed) is removed by evaporation or distillation at reduced pressures and appropriate temperatures. If desired, recrystallization of the crude residue may be effected from a suitable solvent such as acetic acid, benzene, acetone, and the like to yield the pure 4,4'-dioxy-substituted stilbene.

Alternatively, the 4,4'-dioxy-substituted stilbene products (especially 4,4'-dimethoxystilbene) is isolated by simply cooling the reaction mixture sufficiently to induce crystallization (with ambient temperatures usually being sufficient) and collecting the resultant crystals. The crystalline product can then be simply washed with water and dried under vacuum, or, in the alternative, recrystallized from a suitable solvent as described hereinabove to yield the pure 4,4'-dioxy-substituted stilbene.

Instead of being isolated as the free 4,4'-dioxy-substituted stilbene when the oxy-substituents are hydroxy groups, the product is alternatively isolated as the corresponding diacyloxy compound. The crude product is treated with an appropriate acylating agent, for example, acetic anhydride (or a mixture of acetic anhydride and glacial acetic acid) and the like, and heated at an appropriate temperature for a time sufficient to smoothly convert the free 4,4'-dioxy-substituted stilbene, for example, 4,4'-dihydroxystilbene, to the corresponding 4,4'-diacyloxystilbene. The crystalline solid which results upon cooling the reaction solution is collected, usually by suction filtration, washed, and dried. Recrystallization, if desired, may be effected from a suitable solvent such as acetic acid, benzene, acetone, and the like to yield the pure product.

It will be noted that since the diacyloxy derivatives of 4,4'-dihydroxystilbenes are esters, the corresponding free 4,4'-dihydroxystilbene can, if desired, be readily recovered therefrom by standard and conventional procedures.

Thus the present invention provides a convenient synthetic route from 1,1-bis(4-oxy-substituted aryl)-2-haloethanes which can be prepared from appropriate oxy-substituted arenes and monohaloacetaldehydes according to the example set forth hereinbelow or according to procedures described in the prior art, for example, Seiber, U.S. Pat. No. 3,624,162) to 4,4'-dioxy-substituted stilbenes.

It will be further noted that the 4,4'-dioxy-substituted stilbenes, being substituted ethylene compounds, can be hydrogenated, if desired, to the corresponding 1,2-bis(4-oxy-substituted aryl)ethane. For example, 4,4'-dihydroxystilbene can be readily converted to 1,2-bis(4-hydroxyphenyl)ethane, commonly known as bisphenol E or simply BPE.

BPE may also be produced from 3,5,3',5'-tetra-t-butyl-4,4'-dihydroxystilbene. Hydrogenation of the unsaturated ethylene bond followed by removal of the t-butyl groups (debutylation) via standard procedures—for example, heating in an inert and relatively high boiling solvent such as m-xylene, tetralin, and the like in the presence of a catalytic amount of an arenesulfonic acid such as benzenesulfonic acid, p-toluenesulfonic acid, and the like. It will be noted that the isobutene generated during the debutylation reaction can be reacted with phenol to give 2,6-di-t-butylphenol.

The following examples illustrate the present invention and the manner by which it can be practiced.

EXAMPLE 1

Procedure A - To a 1-liter jacketed resin kettle equipped with a mechanical stirrer, gas dispersion tube and thermometer, and cooled to −5° C. with circulating trichloroethylene thermostated cooling liquid, was charged 250 grams (2.9 moles) of vinyl acetate (inhibited with 300 parts per million diphenylamine). Chlorine gas (230.0 grams, 3.2 moles; calculated 207.0 grams, 2.9 moles) was bubbled into the stirred solution from a preweighed lecture bottle over a 4.5-hour period at a rate to maintain the reaction mixture's temperature at about 15° C. (approximately 500 milliliters per minute flow rate). A precipitate initially formed in the reaction mixture but dissolved after about 1 hour. After the 4.50-hour period, the vinyl acetate was completely consumed, as determined via nuclear magnetic resonance spectroscopy.

Nuclear magnetic resonance spectroscopic analysis of the product mixture showed the presence of 1,2-dichloroethyl acetate, chloroacetaldehyde, acetyl chloride, and unidentified derivatives of chloroacetaldehyde.

The crude 1,2-dichloroethyl acetate thus obtained was transferred to a 5-liter flask equipped with a mechanical stirrer and thermometer, and cooled in an ice bath. Absolute ethanol (401.0 grams, 8.7 moles) was added to the stirred, cooled mixture over a 40-minute period at a rate sufficient to keep the temperature below 25° C. The first 30 percent of the addition was slow as the reaction is initially exothermic; the remaining 70 percent was added more quickly. The solution was allowed to stand, with stirring, at ambient temperatures overnight (about 16 hours), and thereafter heated under reflux for a total of 3.5 hours. The reaction mixture was cooled to ambient temperatures to yield 790 grams (56 percent pure) of crude chloroacetal solution.

The hydrogen chloride gas from the refluxing reaction mixture was trapped in water and titrated to the neutral point with 80.0 grams (2.0 moles) of solid sodium hydroxide. Therefore, of the original 881.0 grams charged, 863.0 grams or 98 percent was recovered.

EXAMPLE 2

To a 1-liter jacketed flask equipped with a mechanical stirrer, thermometer, and dropping funnel, and cooled to 0° C. with circulating trichloroethylene thermostated cooling liquid was charged 226.0 grams (2.4 moles) of anhydrous phenol and 200 milliliters of glacial acetic acid. Gaseous hydrogen chloride (21.0 grams, 0.58 mole) was bubbled into the stirred solution, cooled to 0° C. from a pre-weighed cylinder over a 30-minute period. To the stirred solution was added 109.0 grams (0.40 mole) of crude chloroacetal solution from EXAMPLE 1 above over a 1.67-hour period. The solution was maintained at a temperature of 0±0.5° C. and stirred an additional 6 hours, for a total of 7.67 hours. Gaseous nitrogen was then bubbled through the solution, with stirring, to remove any remaining hydrogen chloride. The reaction mixture was added to a hot solution (85° C.) of 50.0 grams (1.25 moles) of sodium hydroxide dissolved in 500 milliliters of glacial acetic acid, whereupon the overall temperature decreased to 60° C. The combined solutions were allowed to stand overnight (approximately 16 hours) and thereafter heated to boiling (approximately 115° C.). Distillate was collected until the distillation vessel temperature reached 120° C.—about 1 hour. The solution remaining in the distillation vessel was heated at reflux for 3 hours, cooled, and concentrated on a rotary evaporator at water pump pressure, then at high vacuum. The remaining residue was treated with a solution of 163 grams (1.6 moles) of acetic anhydride and 200 milliliters of glacial acetic acid, refluxed for 1 hour, and cooled to induce crystallization. The crystals were collected by suction filtration, washed successively with two 50-milliliter portions of acetic acid and two 500-milliliter portions of water, and dried to yield 30.1 grams (25.4 percent based on 0.40 mole of chloroacetal) of 4,4'-diacetoxystilbene, which identity was confirmed by nuclear magnetic resonance spectroscopy.

EXAMPLE 3

The reaction apparatus and conditions described in EXAMPLE 2 above were employed. Anhydrous phenol (226.0 grams, 2.4 moles) dissolved in 200 milliliters of glacial acetic acid was charged to the reaction flask, followed by 56.4 grams (0.58 mole) of sulfuric acid dissolved in 50 milliliters of glacial acetic acid. To the stirred solution, maintained at 0±0.5° C., was added 109.0 grams (0.40 mole) of crude chloroacetal (EXAMPLE 1) over a 1.75 hour period. The reaction mixture was maintained at a temperature of 0±0.5° C. and stirred an additional 6.25 hours, for a total of 8 hours. At the end of the 8-hour reaction period, the reaction mixture was added to a hot solution (85° C.) of 75.0 grams (1.88 moles) of sodium hydroxide in 600 milliliters of glacial acetic acid whereupon the overall temperature decreased to 60° C. The product was isolated as described in EXAMPLE 2 above to yield 90.0 grams of unreacted phenol and 63.5 grams (53.6 percent based on 0.40 mole of chloroacetal) of pure 4,4'-diacetoxystilbene, which purity and identity were confirmed, respectively, by gas chromatography and nuclear magnetic resonance spectroscopy.

EXAMPLE 4

The procedure described in EXAMPLE 3 above was repeated with the exception that 28.2 grams (0.29 mole) of sulfuric acid dissolved in 25 milliliters of glacial acetic acid and 50.0 grams (1.25 moles) of sodium hydroxide dissolved in 500 milliliters of glacial acetic acid were employed. Isolation of the product resulted in the recovery of 139.0 grams of unreacted phenol and a yield of 51.0 grams (43.1 percent based on 0.40 mole of chloroacetal) of pure 4,4'-diacetoxystilbene.

EXAMPLE 5

To a 500-milliliter jacketed flask equipped with a mechanical stirrer, thermometer, and dropping funnel, and cooled to approximately 2° C. with circulating trichloroethylene thermostated cooling liquid, was charged 43.2 grams (0.40 mole) of anisole and 30.6 grams (0.20 mole) of commercial chloroacetal. To the cooled and stirred solution was added a solution of 80.0 grams (0.82 mole) of concentrated sulfuric acid dissolved in 50 milliliters of glacial acetic acid over a 1.17-hour period (1 hour and 10 minutes) at a rate sufficient to maintain the temperature at less than 15° C. When the addition was complete, the solution was stirred an additional 10 minutes, allowed to warm to 15° C. and poured into 1 liter of an ice/water mixture. The mixture was extracted with three 150-milliliter portions of diethyl ether, washed successively with three 100-milliliter portions of saturated aqueous sodium carbonate and three 100-milliliter portions of cold water, and dried over anhydrous sodium sulfate. Evaporation of the ether in vacuo yielded 55.0 grams (almost quantitative) of crude 1,1-bis(4-methoxyphenyl)-2-chloroethane as a colorless oil.

EXAMPLE 6

To a 1-liter glass lined Parr bomb containing a solution of 10.0 grams (0.12 mole) of anhydrous sodium acetate dissolved in 150 milliliters of glacial acetic acid was added 27.5 grams (0.099 mole) of the crude 1,1-bis(4-methoxyphenyl)-2-chloroethane. The bomb was flushed and thereafter pressurized to 100 psig with dry nitrogen. The contents were heated, with stirring, to 200° C. over a 30-minute period. The reaction mixture was maintained at 200° C. for 4 hours and then allowed to cool overnight (approximately 16 hours). The solid material which had crystallized was collected by suction filtration and identified as 4,4'-dimethoxystilbene by gas chromatography. The crystals were placed in a Soxhlet extractor and extracted with 500 milliliters of refluxing benzene over a 3-day period. The crystalline mass which separated upon cooling was collected by suction filtration and dried to yield 12.7 grams of pure product. An additional 2.3 grams of product was collected by concentrating the mother liquor. Total yield, 15.0 grams (63 percent) of pure 4,4'-dimethoxystilbene.

The reaction mixture filtrate contained an unidentified compound believed to be an isomer of 4,4'-dimethoxystilbene.

EXAMPLE 7

The apparatus and procedure described in EXAMPLE 6 above was repeated with the exception that the reaction mixture was heated to 200° C. over a 30-minute period, maintained at that temperature for an additional hour, and allowed to cool over a 2-hour period. The product was collected by suction filtration, washed with 300 milliliters of hot water in a beaker, filtered, and dried under vacuum to yield 15.4 grams (64.8 percent) of 4,4'-dimethoxystilbene as pale tan crystals, melting point, 211°–212° C.

The acetic acid filtrate was evaporated in vacuo to leave a dark brown oil. The oil was mixed with 200 milliliters of water and extracted with 200 milliliters of diethyl ether. The ethereal solution was washed with saturated aqueous sodium carbonate, dried, and evaporated. The resultant oil was taken up in methanol and saturated with diethyl ether to yield a solid material containing only aromatic and methoxy groups as determined by nuclear magnetic resonance spectroscopy.

EXAMPLE 8

The apparatus described in EXAMPLE 5 above was employed.

To a mechanically stirred mixture of 43.2 grams (0.40 mole) of anisole and 39.4 grams (0.20 mole) of commercial bromoacetal cooled to approximately 4° C. was added dropwise a solution of 80.0 grams (0.82 mole) of concentrated sulfuric acid dissolved in 50 milliliters of glacial acetic acid over a 40-minute period at a rate sufficient to maintain the temperature at less than 10° C. (The reaction was more vigorous than the same reaction employing chloroacetal.)

Gas chromatographic analysis of the crude product reaction mixture showed approximately 3.3 grams of unreacted anisole.

The product, 1,1-bis(4-methoxyphenyl)-2-bromoethane, was isolated as described in EXAMPLE 5 above to yield 66.0 grams of colorless oil.

EXAMPLE 9

The Parr bomb described in EXAMPLE 6 above was employed. To a solution of 20.0 grams (0.24 mole) of anhydrous sodium acetate dissolved in 200 milliliters of glacial acetic acid was added the entire crude 1,1-bis(4-methoxyphenyl)-2-bromoethane (66.0 grams, 0.21 mole based on pure product) from EXAMPLE 8 above. The bomb was flushed and then pressurized to 110 psig with dry nitrogen. The contents were heated, with stirring, to 190° C. over a 30-minute period, maintained at that temperature for 1 hour, and allowed to cool over a 2-hour period. The solid which crystallized was collected by suction filtration, washed successively with 50 milliliters of acetic acid, followed by 300 milliliters of warm water in a beaker. The crystalline material was collected and dried under vacuum to yield 33.3 grams (69.4 percent based on bromoacetal employed in EXAMPLE 8 above) of 4,4'-dimethoxystilbene.

Gas chromatographic analysis of the mother liquor indicated that it contained approximately 8.0 grams of unidentified compound.

EXAMPLE 10

To a 500-milliliter jacketed flask equipped with a mechanical stirrer, thermometer, and dropping funnel was charged a solution of 41.2 grams (0.20 mole) of 2,6-di-t-butylphenol dissolved in 50 milliliters of glacial acetic acid and 16.8 grams (0.11 mole) of commercial chloroacetal. To the stirred solution was added 20.0 grams (0.20 mole) of concentrated sulfuric acid, whereupon the temperature increased to approximately 48° C. After approximately 20 minutes of stirring, solid material began to separate from the solution. The reaction mixture was stirred an additional 2 hours and thereafter cooled to ambient temperatures. Approximately 50 milliliters of glacial acetic acid was added to the thick pasty reaction mixture and the solid material collected by suction filtration. The collected solid material was stirred with 500 milliliters of cold water, filtered, and dried to yield 41.4 grams (88 percent) of 1,1-bis(3,5-di-t-butyl-4-hydroxphenyl)-2-chloroethane.

EXAMPLE 11

To a 100 milliliter round-bottomed flask equipped with a magnetic stirrer and a reflux condenser capped with a paraffin-sealed gas bubbler was added 9.45 grams (0.022 mole) of 1,1-bis(3,5-di-t-butyl-4-hydroxyphenyl)-2-chloroethane (from EXAMPLE 10 above), 20 milliliters of glacial acetic acid, and 2.0 grams (0.024 mole) of anhydrous sodium acetate. The mixture was stirred and heated to reflux for 4 hours. The resulting homogeneous solution was cooled to ambient temperatures to induce crystallization of the product. The precipitated solid material was collected by suction filtration, washed successively with acetic acid and water, and dried to yield 7.8 grams (90 percent) of 3,5,3',5'-tetra-t-butyl-4,4'-dihydroxystilbene, which identify was confirmed by nuclear magnetic resonance spectroscopy.

The 4,4'dioxy-substituted stilbene products, particularly the 4,4'-dihydroxstilbenes and the 4,4'-dialkoxystilbenes, exhibit estrogenic activity. They, therefore, have a definite importance in biology, physiology, and biochemistry.

They may also, as noted hereinabove, serve as intermediates in the preparation of 1,2-bis(4-oxy-substituted aryl)-ethanes which have many and varied utilities. For example, they are useful as bactericides, chemical intermediates, monomer units for copolymers, and antioxidants. They are used to stabilize such materials as animal and vegetable fats or oils, gasoline, lubricants, polyalkenes such as polyethylene and polypropylene, and both natural and synthetic rubber. They are also used in the preparation of resins, for example, polyesters, polycarbonates, and the like resins, wherein they are used as the dihydroxy compound which is reacted with phosgene, dibasic acids, dibasic acid halides, and the like.

While the invention has been described with respect to various specific examples and embodiments thereof, it will be understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the preparation of 4,4'-dioxy-substituted stilbenes which comprises heating an acidic reaction medium comprising a 1,1-bis(4-oxy-substituted aryl)-2-haloethane dissolved in a solution of an aliphatic carboxylic acid and a soluble acid salt to a temperature between about 100° C. and about 250° C., and for a time, sufficient to cause dehydrohalo-genation-rearrangement of the 1,1-bis(4-oxy-substituted aryl)-2-haloethane to yield the 4,4'-dioxy-substituted stilbene, with the aforesaid 1,1-bis(4-oxy-substituted aryl)-2-haloethanes being represented by the formula:

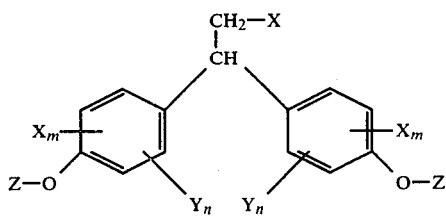

in which X independently represents a halogen selected from the group consisting of chlorine, bromine, and iodine; Y independently represents a non-interfering hydrocarbyl group; Z represents hydrogen or Y; and m and n each independently represent an integer from zero (0) to 4, inclusive, with the proviso that the sum of m and n, with respect to each aryl ring, does not exceed 4.

2. The process of claim 1 wherein the 1,1-bis(4-oxy-substituted aryl)-2-haloethane is a 1,1-bis(4-hydroxyaryl)-2-haloethane and the 4,4'-dioxy-substituted stilbene product is a 4,4'-dihydroxystilbene.

3. The process of claim 2 wherein the 1,1-bis(4-hydroxyaryl)-2-haloethane is 1,1-bis(4-hydroxyphenyl)-2-chloroethane and the 4,4'-dihydroxystilbene is 4,4'-dihydroxystilbene.

4. The process of claim 2 wherein the 1,1-bis(4-hydroxyaryl)-2-haloethane is 1,1-bis(3,5-di-t-butyl-4-hydroxyphenyl)-2-chloroethane and the 4,4'-dihydroxystilbene is 3,5,3',5'-tetra-t-butyl-4,4'-dihydroxystilbene.

5. The process of claim 1 wherein the 1,1-bis(4-oxy-substituted aryl)-2-haloethane is a 1,1-bis(4-alkoxyaryl)-2-haloethane and the 4,4'-dioxy-substituted stilbene is a 4,4'-dialkoxystilbene.

6. The process of claim 5 wherein the 1,1-bis(4-alkoxyaryl)-2-haloethane is 1,1-bis(4-methoxyphenyl)-2-chloroethane selected from the group consisting of 1,1-bis(4-methoxyphenyl)-2-bromoethane and 1,1-bis(4-methoxyphenyl)-2-iodoethane, and the 4,4'-dialkoxystilbene is 4,4'-dimethoxystilbene.

7. The process of claim 1 wherein the aliphatic carboxylic acid is substantially anhydrous.

8. The process of claim 7 wherein the aliphatic carboxylic acid comprises $C_2$ to $C_6$ aliphatic carboxylic acids.

9. The process of claim 8 wherein the $C_2$ to $C_6$ aliphatic carboxylic acid is acetic acid.

10. The process of claim 1 wherein the carboxylic acid salt is pre-formed.

11. The process of claim 10 wherein the pre-formed carboxylic acid salt is an alkali metal carboxylic acid salt.

12. The process of claim 11 wherein the alkali metal carboxylic acid salt is sodium acetate.

13. The process of claim 1 wherein the carboxylic acid salt is formed in situ from the aliphatic carboxylic acid and added hydroxide ion-containing compound.

14. The process of claim 13 wherein the added hydroxide ion-containing compound is an alkali metal hydroxide and the carboxylic acid salt is an alkali metal carboxylic acid salt.

15. The process of claim 14 wherein the alkali metal hydroxide is sodium hydroxide, the aliphatic carboxylic acid is acetic acid, and the alkali metal carboxylic acid salt is sodium acetate.

16. The process of claim 1 wherein the dehydrohalogenation-rearrangement of the 1,1-bis(4-oxy-substituted aryl)-2-haloethane is conducted under an inert atmosphere.

17. The process of claim 16 wherein the inert atmosphere is nitrogen.

18. The process of claim 1 wherein the dehydrohalogenation-rearrangement of the 1,1-bis(4-oxy-substituted aryl)-2-haloethane is conducted at super atmospheric pressures.

19. The process of claim 18 wherein the super atmospheric pressures range between about 75 psig to about 150 psig.

20. The process of claim 1 wherein the time sufficient to cause dehydrohalogenation-rearrangement of the 1,1-bis(4-oxy-substituted aryl)-2-haloethane is between about 0.5 hours and about 5 hours.

21. The process of claim 1 wherein the concentration of the 1,1-bis(4-oxy-substituted aryl)-2-haloethane in the acidic reaction medium is between about 0.2 molar and about 2.0 molar and the gram-equivalent weight ratio of metal carboxylic acid salt to be 1,1-bis(4-oxy-substituted aryl)-2-haloethane is at least 1:1.

* * * * *